(12) United States Patent
Smith et al.

(10) Patent No.: US 7,050,981 B2
(45) Date of Patent: *May 23, 2006

(54) DATA HEALTH MONITOR FOR FINANCIAL INFORMATION COMMUNICATIONS NETWORKS

(75) Inventors: Christina Smith, Croydon (GB); Steve John Harwood Fletcher, Swilland Ipswich (GB); Stephen G. Dale, Stansted Mountfitchet (GB)

(73) Assignee: Reuters Limited (GB)

( * ) Notice: Subject to any disclaimer, the term of this patent is extended or adjusted under 35 U.S.C. 154(b) by 132 days.

This patent is subject to a terminal disclaimer.

(21) Appl. No.: 10/602,761

(22) Filed: Jun. 25, 2003

(65) Prior Publication Data

US 2004/0039671 A1  Feb. 26, 2004

Related U.S. Application Data

(63) Continuation of application No. 09/466,774, filed on Dec. 20, 1999, now Pat. No. 6,587,840, which is a continuation of application No. 08/925,586, filed on Sep. 8, 1997, now Pat. No. 6,006,206.

(51) Int. Cl.
*G06Q 99/00* (2006.01)
*G06Q 40/00* (2006.01)
*G06F 12/00* (2006.01)
*G06F 17/30* (2006.01)
*G06F 15/00* (2006.01)

(52) U.S. Cl. .......................... 705/1; 705/35; 707/203; 715/511; 715/530; 709/224; 709/248

(58) Field of Classification Search ............ 705/1, 705/35, 37; 707/1, 10, 104.1, 200, 203; 715/511, 530, 540; 709/205, 224, 248
See application file for complete search history.

(56) References Cited

U.S. PATENT DOCUMENTS

| | | | |
|---|---|---|---|
| 3,801,961 A | 4/1974 | Coombe | 345/23 |
| 4,371,871 A | 2/1983 | Adams | 340/825.26 |
| 4,584,643 A | 4/1986 | Halpern et al. | 709/248 |
| 4,710,926 A | 12/1987 | Brown et al. | 714/4 |

(Continued)

FOREIGN PATENT DOCUMENTS

EP  0 434 224  11/1990

(Continued)

OTHER PUBLICATIONS

Anonymous, "Bits and PCs", PC User, No. 145, p. 119, Nov. 7, 1990.

(Continued)

*Primary Examiner*—Nicholas D. Rosen
(74) *Attorney, Agent, or Firm*—Banner & Witcoff, Ltd.

(57) ABSTRACT

A financial communications network incorporating a data health monitor is provided that includes a plurality of data sources, a plurality of data collection systems, a client site terminal and a network connecting these components. Each data collection system includes a processor for receiving and formatting financial data received from the data sources, wherein the formatted financial data has a data field including a first data source identifier identifying the data source of the formatted financial data and a first system identifier identifying the data collection system formatting the formatted financial data. The collection system also includes a status code generator for generating and transmitting a status code, and a heartbeat signal generator for generating and periodically transmitting a heartbeat signal. Based on information in data fields, status codes, and heartbeat signal, client site terminals select a real-time or stale display mode for displaying the financial data.

16 Claims, 5 Drawing Sheets

U.S. PATENT DOCUMENTS

| | | | |
|---|---|---|---|
| 4,745,559 A | 5/1988 | Willis et al. | 705/37 |
| 4,750,135 A | 6/1988 | Boilen | 709/231 |
| 4,807,224 A | 2/1989 | Naron et al. | 370/218 |
| 4,868,866 A | 9/1989 | Williams, Jr. | 707/9 |
| 5,077,665 A | 12/1991 | Silverman et al. | 705/37 |
| 5,136,501 A | 8/1992 | Silverman et al. | 705/37 |
| 5,187,787 A | 2/1993 | Skeen et al. | 719/314 |
| 5,195,031 A | 3/1993 | Ordish | 705/37 |
| 5,257,369 A | 10/1993 | Skeen et al. | 719/312 |
| 5,313,461 A | 5/1994 | Ahl et al. | 370/349 |
| 5,396,587 A | 3/1995 | Reed et al. | 715/503 |
| 5,442,637 A | 8/1995 | Nguyen | 714/708 |
| 5,471,629 A | 11/1995 | Risch | 707/201 |
| 5,483,631 A | 1/1996 | Nagai et al. | 715/736 |
| 5,485,455 A | 1/1996 | Dobbins et al. | 370/255 |
| 5,491,780 A | 2/1996 | Fyles et al. | 715/733 |
| 5,519,704 A | 5/1996 | Farinacci et al. | 370/402 |
| 5,541,927 A | 7/1996 | Kristol et al. | 370/408 |
| 5,557,798 A | 9/1996 | Skeen et al. | 705/35 |
| 5,577,608 A | 11/1996 | Hanson et al. | 206/386 |
| 5,581,703 A | 12/1996 | Baugher et al. | 709/225 |
| 5,581,704 A | 12/1996 | Barbara et al. | 711/141 |
| 5,590,269 A | 12/1996 | Kruse et al. | 705/9 |
| 5,617,522 A | 4/1997 | Peltier | 715/763 |
| 5,617,541 A | 4/1997 | Albanese et al. | 709/207 |
| 5,631,907 A | 5/1997 | Guarneri et al. | 370/474 |
| 5,634,004 A | 5/1997 | Gopinath et al. | 710/317 |
| 5,694,608 A | 12/1997 | Shostak | 715/506 |
| 5,701,465 A | 12/1997 | Baugher et al. | 707/10 |
| 5,704,042 A | 12/1997 | Hester et al. | 709/204 |
| 5,706,435 A | 1/1998 | Barbara et al. | 711/141 |
| 5,706,510 A | 1/1998 | Burgoon | 707/203 |
| 5,793,366 A | 8/1998 | Mano et al. | 715/839 |
| 5,794,206 A | 8/1998 | Wilkinson et al. | 705/1 |
| 5,799,318 A | 8/1998 | Cardinal et al. | 707/101 |
| 5,826,253 A | 10/1998 | Bredenberg | 707/2 |
| 5,835,910 A | 11/1998 | Kavanagh et al. | 707/103 R |
| 5,838,938 A | 11/1998 | Morgan | 715/723 |
| 5,925,105 A | 7/1999 | Hales, II et al. | 709/233 |
| 5,943,675 A | 8/1999 | Keith et al. | 707/201 |
| 5,946,689 A | 8/1999 | Yanaka et al. | 707/10 |
| 5,982,890 A | 11/1999 | Akatsu | 707/200 |
| 5,995,981 A | 11/1999 | Wikstrom | 707/202 |
| 6,006,206 A | 12/1999 | Smith et al. | 705/35 |
| 6,078,930 A | 6/2000 | Lee et al. | 707/202 |
| 6,085,244 A | 7/2000 | Wookey | 709/224 |
| 6,112,015 A | 8/2000 | Planas et al. | 709/223 |
| 6,292,828 B1 | 9/2001 | Williams | 709/218 |
| 6,574,234 B1* | 6/2003 | Myer et al. | 370/462 |
| 6,587,840 B1 | 7/2003 | Smith et al. | 705/35 |
| 2002/0120648 A1* | 8/2002 | Ball et al. | 707/511 |

FOREIGN PATENT DOCUMENTS

WO      WO 93/23958      11/1993

OTHER PUBLICATIONS

Anonymous, "Lead Story: Rocky Road For Micrognosis System At Nomura" Merit Hobbled, Telerate Certification Lags, Trading Systems Technology, vol. 6, No. 11, Nov. 30, 1992.

Anonymous, "CSK Pushes Real-time Market Data Over The Internet", Multimedia Business Analyst, No. 8, p. 8, Feb. 12, 1997.

Paulus, "Well Speculated", http://www.slingshot.ie/press/global.htm, Aug. 1997.

* cited by examiner

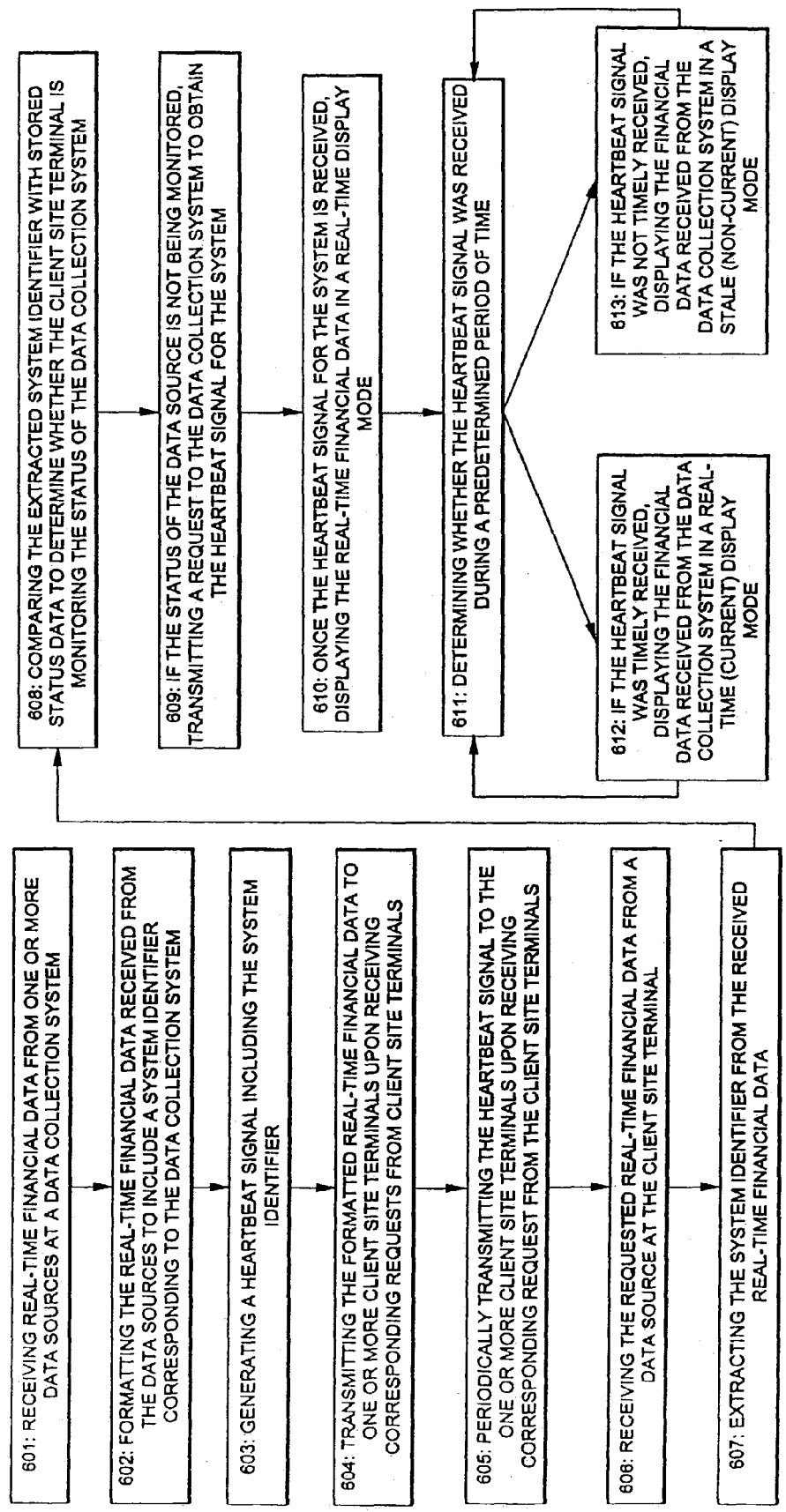

DATA HEALTH MONITOR FOR FINANCIAL INFORMATION COMMUNICATIONS NETWORKS

FIELD OF THE INVENTION

The present invention relates to a data health monitor for financial information communications networks which automatically detects problems in the delivery of real-time financial information to client site computer systems, which problems may result in the use of non-current financial information by the client site computer systems. Upon detection of a delivery problem, the data health monitor according to the present invention automatically alerts users at the client site computer system that the financial information being used is not real-time and automatically clears the alert when the used information becomes real-time. The data health monitor according to the present invention automatically detects problems in the delivery of financial data both from data sources to the communications network and within the communications network itself. Through the use of open architecture, the data health monitor according to the present invention may be applied to a variety of client site applications including a client site terminal with a display displaying the financial information and an indication whether the information is real-time or stale.

BACKGROUND OF THE INVENTION

Reuters delivers financial information from stock exchanges and other markets throughout the world to numerous client site computer systems using an extensive wide area network. The financial information delivered by this network includes financial data concerning instruments such as stocks, bonds, foreign exchange instruments, and commodities which may be traded across the world. Within Reuters network, each financial instrument traded over the network is treated as, a separate entity from the time it is entered onto the network from the financial exchange until it is delivered to the client site computer systems. As trades are carried out on the various financial exchanges, corresponding financial information concerning the financial instrument transactions on the exchanges is delivered to numerous client sites worldwide in real time as updates to each affected instrument.

Approximately 1.5 million financial instruments are updated in real time in the Reuters worldwide network. All financial information should then be available in real time to all client sites worldwide with an interest in the information. Thus, accurate, real-time updates to client sites are important to the real-time display of financial information at the client sites. If the displayed financial information is not current, users of the system may rely upon faulty information in performing financial transactions, resulting in substantial financial losses. Furthermore, the display of stale information by the client sites will reduce the users' confidence in, and therefore use of, the Reuters network.

Further, the types of financial instruments available to users is not fixed. Rather, the number of financial instruments available is constantly growing. However, current systems are designed to service one to few instrument types. By accommodating only a few instrument types, designers have optimized the operation of these closed trading systems. However, as the variety of instrument types increases, these closed systems become obsolete. Also, current systems are designed to be used with specific devices and connections, again limiting their usefulness in a global environment where the predetermined system hardware and software norms may not be available or desired. To this end, interaction between divergent operating systems has been difficult. Further, current trading systems do not readily exchange information with other applications (also referred to as host applications) running on a client site terminal. To this end, the end user is relegated to manually transporting received trading information between applications. However, manually transporting information fails to account for any change in the health (or staleness) of the information. To this end, stale information can otherwise current information as present in a user's end application. For example, a spreadsheet calculating a trader's investment in an instrument may reflect erroneous information when the value of each instrument changes over time and the spreadsheet is unaware of the changes. Accordingly, a need exists to provide a system able to accommodate changing instrument types, operate within different operating systems, and provide information to various other applications running on a client site terminal.

SUMMARY OF THE INVENTION

In view of the risks and consequences associated with the display of stale (not real-time) financial data by the Reuters financial information network, the data health monitor according to the present invention provides a system for automatically detecting and identifying to the users of the network stale, non-current financial information. The data health monitor provides accurate detection and identification of stale financial information in real time to prevent both losses due to user reliance on stale information and loss of user confidence in the Reuters financial information network.

Also, the data health monitor according to the present invention is based on an open system architecture wherein the data health monitor is designed to accommodate new financial instruments. Additionally, the data health monitor according to the present invention is designed to be system independent, so as to accommodate varying operating systems and associated architectures. For example, the data health monitor according to the present invention is cross-platform enabled so that, while a client site terminal may be running at least one variety of operating systems, the client site terminal may still receive and process received information. Contemplated operating systems include Windows 95™, Windows NT™, Windows 3.1, from Microsoft, OS/2 from IBM, the UNIX operating system and the Apple Operating systems, and the like. The program running on each client site terminal receives and interprets information from the network so the information may be used locally, independent of the operating system or combination of hardware/software used. Further, the data health monitor according to the present invention is constructed on an open application architecture which links received information between applications. In the case of Microsoft Wmdows™ operating systems, the data health monitor uses the DDE open data interchange format to enable the transportation of information receive via the data health monitor system to additional applications running on the client site terminal. These additional applications may include spreadsheet programs, databases including knowledge bases, word processing documents, graphs, model, and the like. For example, received information can be ported to an Excel spreadsheet program (by the Microsoft Corporation of Redmond, Wash.) using DDE for various calculations. If the received information is stale (or suspect), the spreadsheet is alerted to the staleness of the received information. In response, the spreadsheet alerts the end user that at least some of the received information is stale. These alerts may take the form of altered screen colors, flashing banners, and the like. In an alternative embodiment, another application (other than the spreadsheet, or other end application) at the client site terminal alerts the user that the received information is stale.

The data health monitor according to the present invention is contemplated to be capable of detecting problems and/or delays in the delivery of financial information 1) from the financial exchanges or other real-time financial information sources to the network and 2) within the network itself Moreover, in the present invention, each financial instrument may be individually marked as stale based upon delivery problems or delays relating to the source of the financial instrument data or problems within the portion of the network which delivers the financial instrument data to the client site computer systems.

A data health monitor in accordance with the present invention includes a processor for receiving real-time financial data from a data source, formatting the real-time financial data to include a data source identifier, and transmitting the formatted real-time financial data onto the communications network The data health monitor also includes a status code generator for generating and transmitting a data source status code based upon the operating status of the data source wherein the data source status code includes the data source identifier. The status code generator automatically updates the data source status code in response to changes in the operating status of the data source and automatically transmits the updated data source status code. A client site computer system receives and processes the formatted real-time financial data, data source status code and the updated data source status code, and selects in real time a stale or real-time identifier (real-time/stale identifier) for the formatted real-time financial data based upon the data source identifier of the formatted real-time financial data, the data source status code and the updated data source status code. The client site computer system then utilizes the formatted real-time financial data in accordance with the selected identification. When applied to a client site terminal, the selected real-time/stale identifier relates to a selected stale or real-time display mode. When the financial information is received, the terminal then displays the financial information in the selected display mode.

Another data health monitor in accordance with the present invention includes a processor for receiving real-time financial data from a data source, formatting the real-time financial data to include a system identifier, and transmitting the formatted real-time financial data onto the communications network. The processor also includes a heartbeat signal generator for generating and transmitting at a predetermined interval a heartbeat signal including the system identifier. A client site computer system receives and processes the formatted real-time financial data and the heartbeat signal, and selects in real time a stale or real-time identifier (real-time/stale identifier) for the formatted real-time financial data based upon the system identifier of the formatted real-time financial data and the heartbeat signal. The client site computer system then uses the formatted real-time financial data in accordance with the selected real-time/stale identifier.

One of the various of the client site computer system implementations is in a terminal with an associated display. Here, a client site terminal receives and processes the formatted real-time financial data and the heartbeat signal, and selects in real time the real-time/stale identifier embodying a stale or real-time display mode for the formatted real-time financial data based upon the system identifier of the formatted real-time financial data and the heartbeat signal. The client site terminal then displays the formatted real-time financial data in accordance with the selected display mode.

A financial communications network incorporating a data health monitor according to the present invention includes a plurality of data sources, a plurality of data collection system, a client site computer system and a network connecting these components.

Each data collection system includes a processor for receiving and formatting financial data received from said data sources, wherein the formatted financial data has a data field including a first data source identifier identifying the data source of said formatted financial data and a first system identifier identifying the data collection system formatting said formatted financial data. The data collection systems also include a status code generator for generating and transmitting a status code, wherein the status code generator automatically updates the status code when the operating status of a corresponding data source changes; and a heartbeat signal generator for generating and periodically transmitting a heartbeat signal.

The client site computer system includes a processor for receiving the formatted financial data, the heartbeat signal and the status codes which it processes to determine whether there is a problem in the receipt of the financial data which prevents the terminal's receipt of the data in real time. The client site computer system then selects a real-time/stale identifier for identifying the financial data, and uses the financial data in accordance with the selected real-time/stale identifier. When a selected application of the client site computer system is a terminal including a display for displaying the financial information, the selected real-time/ stale identifier corresponds to a real-time or stale display mode. In this regard, when displaying the financial data, the terminal displays the financial data in accordance with the selected real-time or stale display mode.

Various additional advantages and features of novelty which characterize the invention are further pointed out in the claims that follow. However, for a better understanding of the invention and its advantages, reference should be made to the accompanying drawings and descriptive matter which illustrate and describe preferred embodiments of the invention.

BRIEF DESCRIPTION OF THE DRAWINGS

FIG. 6 provides a diagram of a method of monitoring the real-time delivery of financial data within the communications network of FIG. 1 based upon a heartbeat signal generated by a data health monitor according to the present invention.

DETAILED DESCRIPTION

The present invention will now be described in detail with reference to the accompanying drawings. While the present invention is described in the context of a communications network including a specific number of components, the data health monitor according to the present invention may be incorporated into networks of many structures and sizes. The drawings are intended to provide one example of a network configuration in which a data health monitor may be implemented and are not intended to limit the applicability of the present invention to other network configurations.

Figure 1:
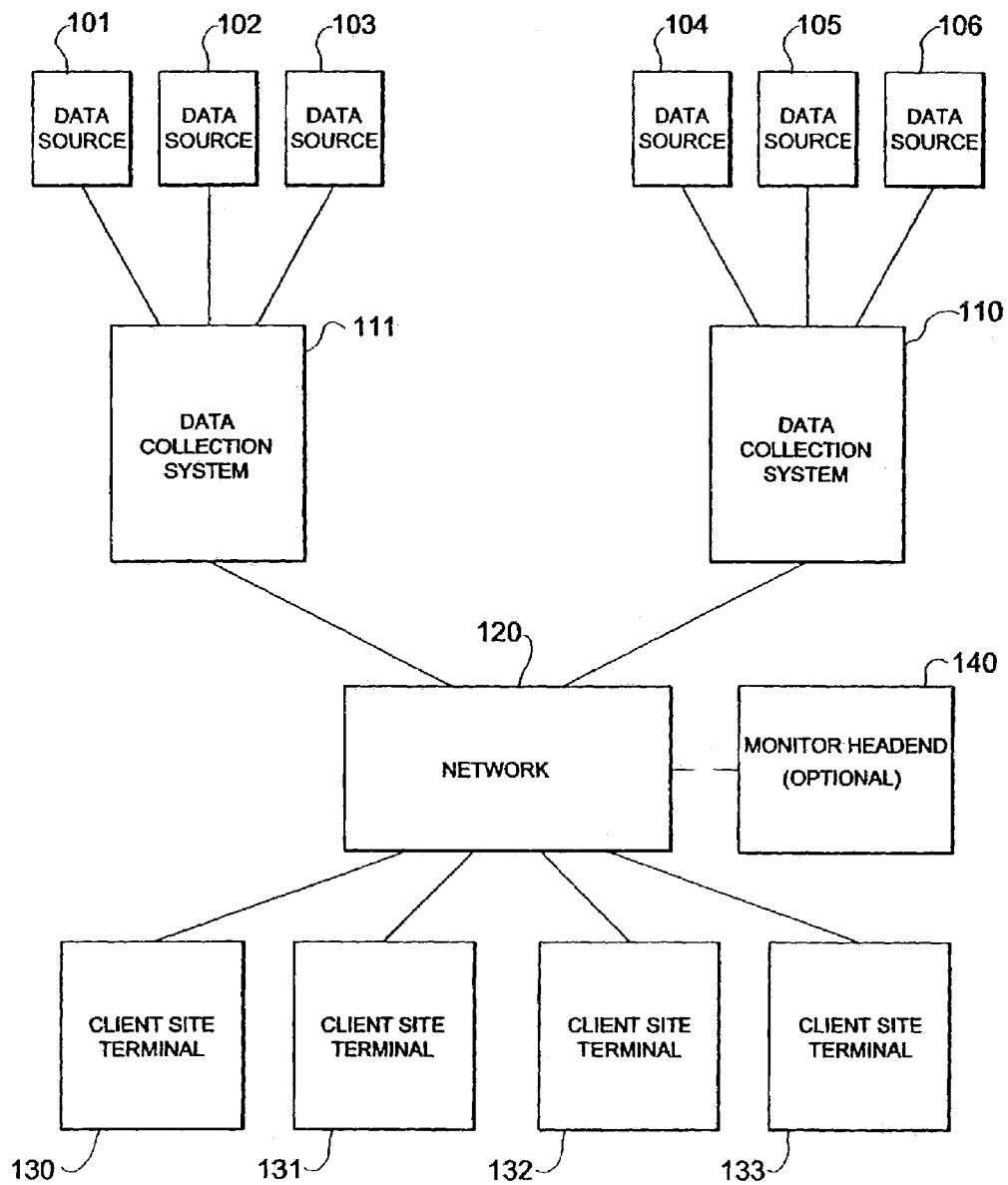
FIG. 1 provides a block diagram of components of a communications network provided with a data health monitor according to the present invention.

As shown in FIG. 1, a financial information communications network incorporating a data health monitor in accordance with the present invention includes a plurality of data sources 101–106 for providing real-time financial data from financial exchanges such as stock markets, commodity markets, foreign exchange markets, etc. as well as financial data from databases and other real-time data sources (generically referred to herein as "data sources").

One or more data collection systems (DCSs), for example, 110 and 111, receive the real-time financial data provided by the data sources 101–106 respectively. Upon receiving the real-time financial data, each DCS formats the received financial data in a predetermined format which may be processed by the client site terminals to enable the client site terminals to display the financial data in real time. The financial data format created by the DCS also includes a data field with a data source identifier identifying the source of the financial data and a system identifier identifying the DCS processing the data. This data field is abbreviated as DSO_ID and is 10 discussed in greater detail below with reference to FIGS. 2 and 4. Once the DCS has appropriately formatted the real-time financial data, it transmits the data via a network 120 to a one or more client site terminals 130–133.

Each DCS also monitors the data feeds from each respective data source from which the DCS receives real-time financial data and generates and stores a data source status code corresponding to each data source. The data source status code for each data source includes a data source identifier and status data to indicate whether the data source is operating in a normal operations mode (real time) or in a problem operation mode. The problem operation mode includes, but is not limited to, errors arising from delayed reception of data or no reception of data (i.e., missing data). The data source identifier in the status code is similar to or matches the data source identifier in the. DSO_ID field of the financial data provided by the corresponding data source. Each data source status code is transmitted to each client site terminal receiving the financial data provided by the respective data source.

When a DCS detects a delay in the delivery of financial data from a data source, the DCS generates and transmits a first status code update signal having a predetermined data value to each client site terminal receiving financial data from the problematic data source. The status code update signal has the same format as the data source status code—it includes a data source identifier and status data. The DCS also stores the status code update as the new data source status code.

Upon receipt of the formatted real-time financial data from one or more DCSs, each client site terminal (e.g., 130–133) automatically extracts and processes the data source identifier from the DSO_ID. If the client site terminal does not already monitor the status code corresponding to the data source identified by the DSO_ID, the client site terminal automatically sends a request for the status code to the appropriate DCS. Upon receiving the status code, the client site terminal displays the financial data having the same data source identifier in accordance with the status indicated by the status code.

Once the client site terminal monitors the status code for financial data from a particular data source, it receives status code updates from the DCS when the operating status of the data source changes. Upon receipt of the first status code update signal indicating a problem with the financial data from the particular data source, the client site terminal automatically compares the data source identification within the DSO_ID of all displayed financial data with the data source identification in the status code update signal and displays as stale any financial data having a matching data source identification.

When the DCS which detected the problematic data source determines that the data source is once again properly providing real-time financial data, the DCS generates and transmits a second status code update having a different status data value than the first status code update. Upon receipt of this second status code update the client site terminal automatically returns the display of the financial data from the corresponding data source to a real-time (not stale) display.

Thus, the data health monitor according to the present invention automatically detects problems and/or delays in the delivery of real-time financial data from data sources such as financial exchanges and automatically notifies users at the corresponding client site terminals that the displayed financial data is stale (not current) when there is a problem with data delivery from one or more of the data sources.

The data health monitor according to the present invention also enables monitoring of the transmission of formatted real-time financial data between each DCS and the client site terminals. Each DCS generates and periodically transmits a "heartbeat" signal to each client site terminal receiving real-time data from the DCS via the network 120. The heartbeat data signal includes a system identifier to identify the DCS generating the heartbeat. The system identifier in the heartbeat signal is similar to or matches the system identifier in the financial data processed by the corresponding DCS. The heartbeat is transmitted to the client site terminals at predetermined intervals, for example, once every thirty seconds.

Each client site terminal receiving real-time financial data from a particular DCS monitors the heartbeat from that DCS. A client site terminal receiving financial data from multiple DCSs monitors the heartbeat from each DCS from which it receives the financial data. If the client site terminal does not receive two heartbeats in a row from a certain DCS, i.e., if no heartbeat signal is received from a DCS, for example, after 60 seconds (one minute), the client site terminal compares the DCS identifier from the missing heartbeats with the DCS identifier in the DSO_ID field of all displayed financial data. When the DCS identifier from the missing heartbeats matches the DCS identifier in the DSO_ID field of displayed financial data, the client site terminal automatically alters the display of the data to indicate that the displayed data is stale.

In this way, the data health monitor according to the present invention monitors the transmission of financial data between the DCSs and the client site terminals and automatically notifies the client site terminal users when the displayed financial data from a specific DCS is not current due to problems within the DCS, the network 120 and/or the client site terminal itself In an alternative embodiment, each data source (101–106) generates a heartbeat signal as well. The heartbeat signals from the data sources are transmitted to DCSs 111 and 110. When the DCSs transmit their heartbeat signals onto network 120, they also transmit the heartbeat signals from their data sources as well. For example, DCS 111 transmits the heartbeat signals from data sources 101–103 to network 120 and DCS 110 transmits the heartbeat signals from data sources 104–106 to network 120. In response the to heartbeat signals from the various data sources, client site computer systems 130–133 are able to monitor the status of each data source of interest independently from the other data sources and independently from the status of each DCS. Accordingly, a client site computer system is contemplated to utilize this greater amount of status information in the computer system's operation. When the computer system includes a terminal displaying the status of piece of financial information, the terminal is contemplated to display the financial information of interest in a stale or real-time mode.

An optional monitor headend 140 may be provided within the network to provide additional information to the client site terminals concerning network problems. For example, the monitor headend 140 may maintain a database which stores information concerning the location, cause, and approximate repair times of all network problems. A user at a client site terminal may access the database to view this information, for example, when the user sees that some displayed financial data is stale or at any time. The monitor headend 140 periodically updates the database and displays to the user the schedule for future updates of the information.

Client site computer systems 130–133 may include additional applications which use the received heartbeat signal to alert a user to the presence of stale information in the applications. For example, client site computer system 130 may include a spreadsheet program receiving current information through a DDE link to an application receiving information over network 120. In response to a missing heartbeat signal or a heartbeat signal noting the staleness of some information, the spreadsheet program alerts a user that the received information is stale or invalid (depending on the actual case of the received information). An advantage of alerting a user to the staleness of information as ported into additional applications includes ensuring that a user knows when information is current and not. Another advantage is that, through alerting a user when information becomes stale (as enabled through monitoring the heartbeat signal), a greater level of confidence in the correctness of received information and calculated information dependent thereon in the end application is instilled.

Figure 2:
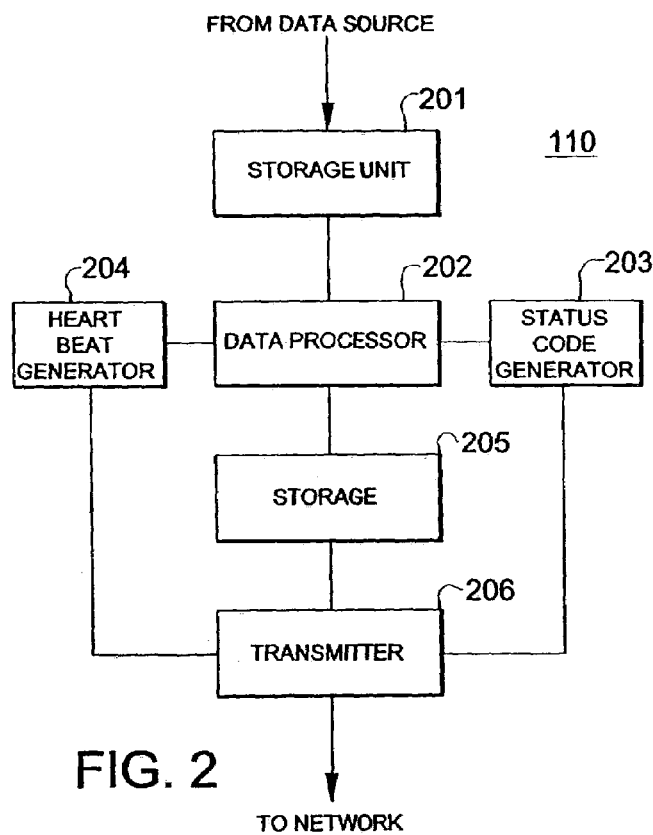
FIG. 2 provides a block diagram of the components of a data collection system for use in the communications network of FIG. 1.

A DCS 110 for use in the network of FIG. 1 is illustrated in FIG. 2. The DCS 110 includes a storage unit 201 for storing real-time financial data received from one or more data sources, for example, data sources 104–106 shown in FIG. 1. A data processor 201 automatically formats the real-time financial data to include a network header field (for example, a sequence number used by the network 120 to' route the data to the client site terminals) and a data source identifier field for identifying the source of the financial data and the DCS that processes the financial data (see FIG. 4). The formatted real-time financial data is then temporarily stored in storage 205 and transmitted by transmitter 206 onto the network 120 for delivery to client site terminals, e.g., client site terminals 130–133 of FIG. 1.

The DCS 110 also includes a status code generator 203 which automatically generates a status code for each data source from which the DCS 110 receives real-time financial data. The status code for each data source includes a header, a source identification field to identify the data source corresponding to the status code, and a status field to indicate the operating status of the respective data source. According to one embodiment of the present invention, the operating status of a data source may be indicated as follows.

If the data source is operating properly, the status field is set to a value of ten thousand or zero (where zero indicates a start up condition or initial value).

If there is a problem with the data source, the status field is set to any value other than ten thousand or zero.

Moreover, the status code header is set to zero (or other invalid header number) to notify each client site terminal that the received data represents a status code. By setting the header to zero, the status code generator 203 within DCS 110 enables client site terminals to differentiate the status codes from other data transmitted within the network having headers with valid header numbers.

As each client site terminal receives financial data originating at a particular data source, the client site terminal automatically requests the current status code of that data source from the DCS 110. Upon receipt of the request by the DCS 110, the processor 202 generates a first control signal to the status code generator which, in response, outputs the current status code for that data source to the requesting client site terminal via transmitter 206.

The processor 202 continuously monitors the receipt of real-time financial data from each data source (e.g., 104–106). When the processor 202 detects a change in the operating status of a data source e.g., 104, 105 or 106), the processor automatically generates a second control signal to the status code generator 203 which in response generates a status code update for the corresponding data source. The status code generator formats the status code update as described above based upon whether there is a problem with the data source or the data source has returned to normal operation. The status code generator 203 then automatically transmits the status code update via transmitter 206 to all client site terminals receiving financial data from the affected data source. The status code generator 203 also automatically stores the status code update as the new status code for that data source.

The DCS 110 further includes a heartbeat generator 204 which generates a heartbeat signal corresponding to the DCS 110 while the DCS is transmitting financial data to the client site terminals. The heartbeat generator automatically transmits the heartbeat signal once every predetermined period of time, for example, once every thirty seconds. Each heartbeat signal includes a system identifier code which identifies the particular DCS. As a result, when a client site terminal (e.g., 130–133) receives financial data from more than one DCS, the client site terminal also periodically receives a heartbeat signal from each DCS. This enables the client site terminal to monitor the connection between the terminal and each DCS to insure real-time transmission of financial data from each DCS to the client site terminal.

The above-described components of DCS 110 may be hardware components, software components, or a combination thereof. Moreover, the components may be integrated into a single processor or distributed among multiple processors as necessary to perform the functions of the DCS 110.

Figure 3:
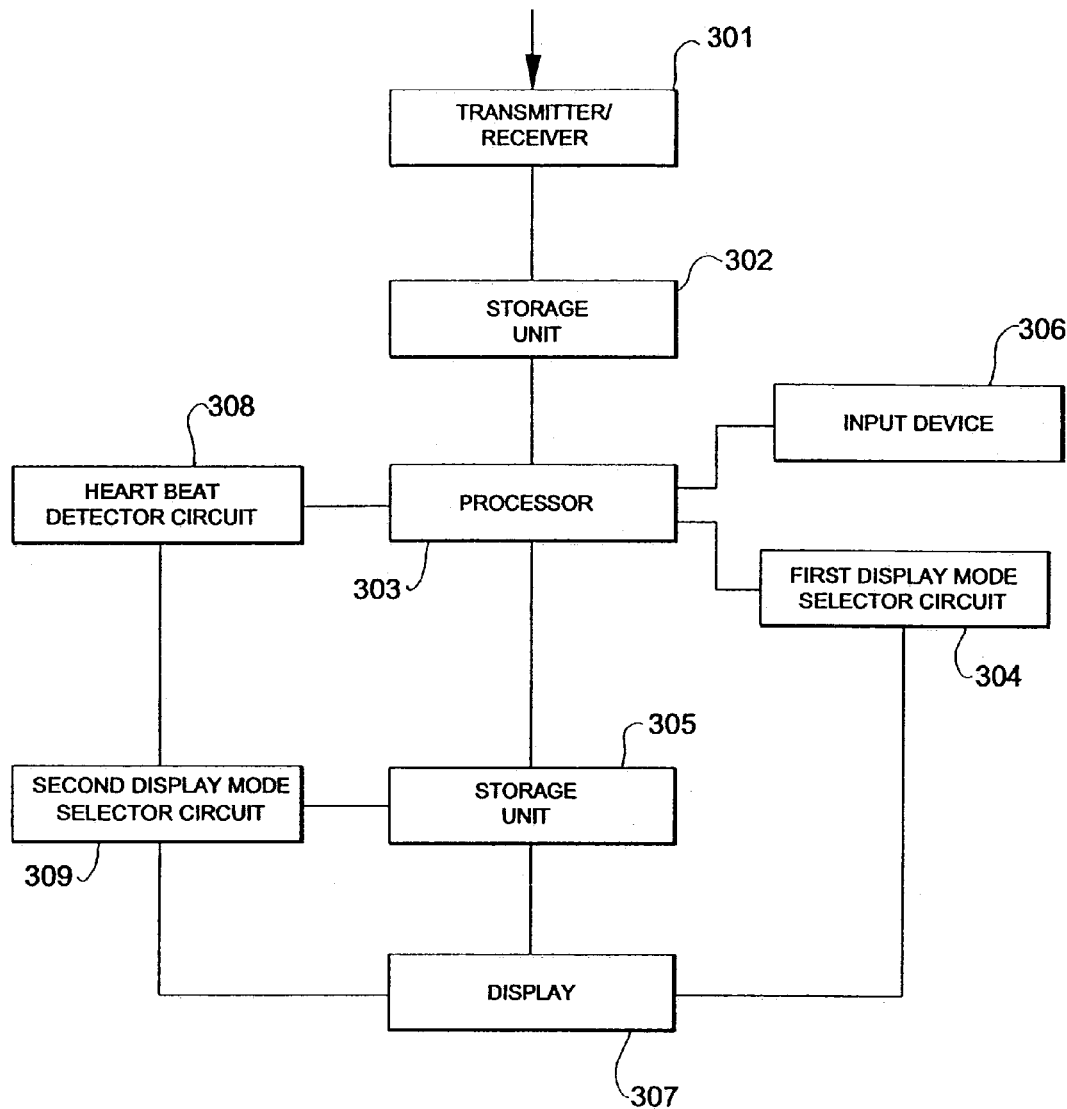
FIG. 3 provides a block diagram of the components of a client site terminal for use in the communications network of FIG. 1.

FIG. 3 provides an illustration of a client site terminal 130 for use in the network of FIG. 1. The client site terminal 130 includes a transmitter/receiver 301, storage units 302 and 305, a processor 303, a first display selector circuit 304, a heartbeat detector circuit 308, a second display mode selector circuit 309, an input device 306 for receiving inputs from the user of the client site terminal, and a display 307 for displaying real-time financial data to the user.

The client site terminal performs at least two types of monitoring to assure that the financial data is accurately displayed to the user as either real-time data or stale data. First, the client site terminal monitors the delivery of financial data from the data sources using the status code outputs from the DCSS. Second, the client site terminal monitors the transmission of the data from the DCS to the client site terminal using the heartbeat signals output by the DCSs.

Monitoring of the data sources is performed as follows. Initially, the client site terminal sends a request for real-time financial data from one or more data sources selected by the user. The DCS associated with each data source requested by the client site terminal receives the request and transmits the corresponding financial data (once formatted as described above with reference to FIG. 2) to the client site terminal.

Upon receipt of formatted real-time financial data from a DCS, the client site terminal stores the data in storage 302. Processor 303 extracts from the data the DSO_ID information identifying the data source and determines whether it is currently monitoring the status of the data source. If the client site terminal is not monitoring the status of the data source, the processor 303 transmits a request to the associated DCS providing the financial data and requests the status code for the data source. The status code generator 203 within the DCS transmits the status code to the client site terminal and also automatically sends subsequent status code updates as they are generated as described above with reference to FIG. 2. The client site terminal stores the status code in storage unit 305. This process enables the client site terminal to monitor the status of the data source.

Once the client site terminal is monitoring the data source of the received financial data, the first display mode selector circuit 304 selects a real-time or stale display mode for the financial data in accordance with the status (real-time or stale) of the data source as indicated by the current status code stored by in the client site terminal in storage unit 305. The first display mode selector circuit outputs a control signal to the display 307, and the display displays the financial data received from the processor 303 in accordance with the control signal from the first display mode selector circuit.

When the client site terminal receives a status code update from a DCS indicating that there is a problem with a data source, the processor 303 extracts the DSO_ID data from the received status code update. The first display mode selector circuit 304 compares the extracted source identifier with the source identifiers of the financial data displayed by display 307. If the DSO_ID field of the displayed data matches the DSO_ID field of the received status code update, the first display mode selector circuit 304 generates another control signal to alter the display of the financial data by display 307 to indicate to the user that the displayed data is stale (not current). For example, stale data may be displayed by changing the color of the displayed data, placing a strike out mark through the stale data, graying out the data, or by any other suitable means. The display of financial data with non-matching DSO_ID fields is unaffected by the receipt of the status code update.

The client site terminal 130 performs its second monitoring function of monitoring of the transmission of financial data from the DCSs to the client site terminal as follows. According to one embodiment of the present invention in which system status monitoring is automatic, the client site terminal automatically requests heartbeat signals from each DCS providing financial data to the terminal when the user of the terminal first requests financial data from the DCS. In other embodiments of the present invention, the system status monitoring function of the client site terminal is not automatic, but is activated either upon receipt of a heartbeat signal from a DCS or manually by the user.

When the client site terminal 130 receives a heartbeat signal from a DCS, the heartbeat detector circuit 308 within the terminal extracts the system identifier data from the heartbeat signal and stores the signal in storage 305. The heartbeat detector circuit 308 repeats this process each time a heartbeat signal from the DCS is received. If the heartbeat detector circuit 308 does not receive a heartbeat within a predetermined period of time (for example, 45 seconds), the second display mode selector circuit 309 compares the system identifier of the missed heartbeat with the system identifier within the DSO_ID field of the financial data displayed by display 307. If the system identifier of displayed financial data matches that of the missed heartbeat, the second display mode selector circuit 309 selects a stale display mode for the financial data and sends a control signal to the display 307 to alter the display of the financial data to indicate that it is stale (non-current). The display of financial data having different system identifiers is not changed. In this manner, the client site terminal monitors the transmission of financial data between the DCSs and the terminal and automatically notifies the user when displayed data is stale due to problems with the DCS, the network 120, and/or the client site terminal itself.

The above-described components of client site terminal 130 may be hardware components, software components, or a combination thereof. Moreover, the components may be integrated into a single processor or distributed among multiple processors as necessary to perform the functions of the client site terminal 130.

Figure 4A:
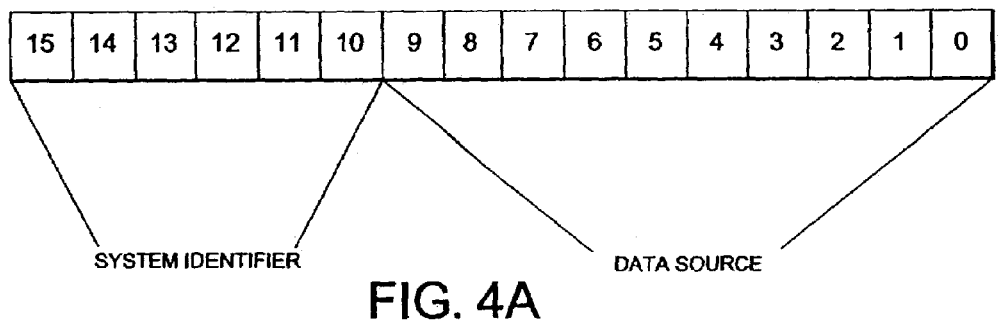
FIGS. 4A and 4B provide diagrams of system identifier and data source identification fields generated by the data health monitor according to the present invention.
Figure 4B:
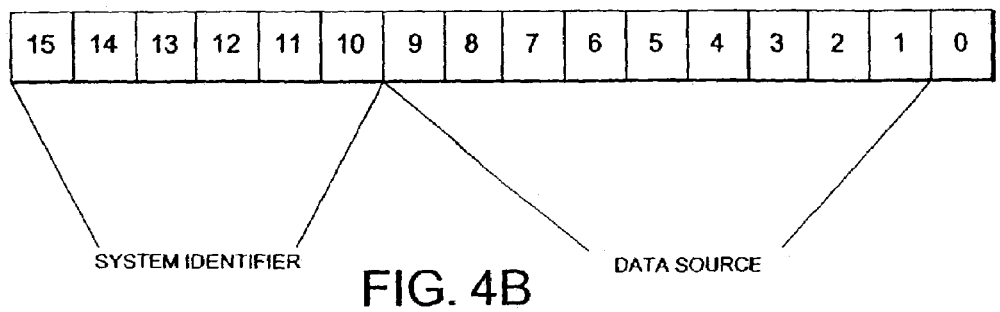

FIGS. 4A and 4B provide a diagram of one format for a DSO_ID field within the formatted financial data transmitted by each DCS. As shown in FIG. 4A, the DSO_ID field may consist of sixteen bits of data arranged in three groups. Bits 0 to 9 store the data source identifier and bits 10 to 15 store the system or DCS identifier. In one embodiment, all bits 0–9 are used to specify the data source. In an alternative embodiment, bit 0 may be left unused or assigned additional functionality as needed to implement the data health monitor according to the present invention within a financial data communications network. As shown in FIG. 4B, less than all bits 1–9 are used to specify the data source and bit 0 is used to alert the client site computer system to disregard the unneeded bits. For example, in the alternative embodiment, if bit 0 is set, then bits 7–9 are ignored and the source is identified through an analysis of bits 1–6.

Embodiments of the present invention also contemplate the DSO_ID field as incorporating greater bit lengths. For example, 32 and 64 bit lengths are contemplated. By the use of these extended lengths, a greater number of data sources are able to be specified.

Figure 5:
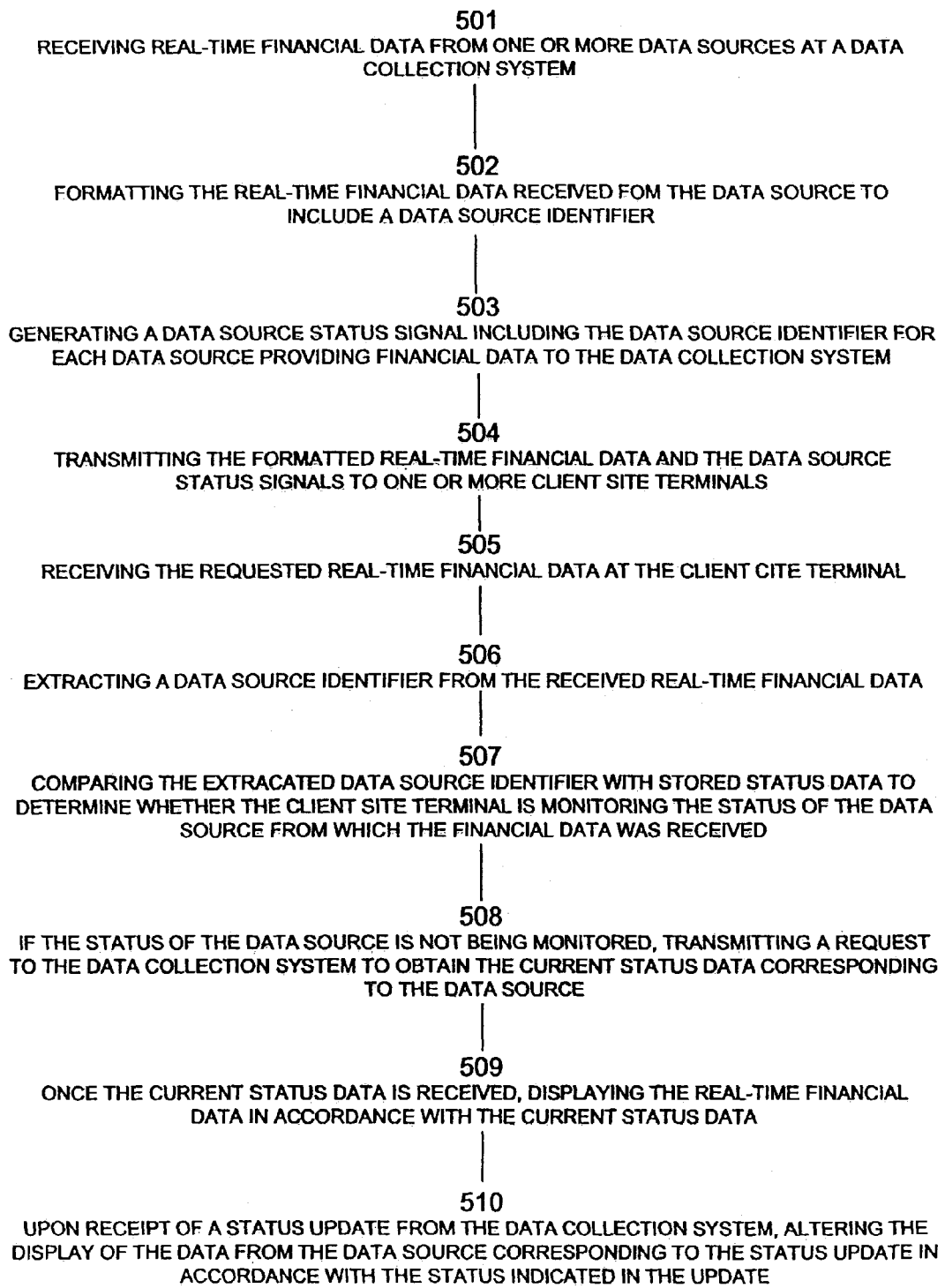
FIG. 5 provides a diagram of a method for monitoring the real-time delivery of financial data from one or more real-time financial data sources based upon data source identification information generated by the data health monitor and provided with the delivered financial data.

FIG. 5 illustrates a method for monitoring the health (real-time availability) of financial data from one or more data sources in accordance with the present invention. This method includes the steps of 501: receiving real-time financial data from one or more data sources at a data collection system;
502: formatting the real-time financial data received from the data sources to include a data source identifier;
503: generating a data source status signal including the data source identifier for each data source providing financial data to the data collection system;
504: transmitting the formatted real-time financial data and the data source status signals to one or more client site terminals upon receiving corresponding requests from the client site terminals;
505: receiving the requested real-time financial data from a data source at the client site terminal;
506: extracting a data source identifier from the received real-time financial data;
507: comparing the extracted data source identifier with stored status data to determine whether the client site terminal is monitoring the status of the data source from which the financial data was received;
508: if the status of the data source is not being monitored, transmitting a request to the data collection system to obtain the current status data corresponding to the data source;
509: once the current status data is received, displaying the real-time financial data in accordance with the current status data (either displaying the data as stale data or real-time data); and
510: upon receipt of a status update from the data collection system, altering the display of the data from the data source corresponding to the status update in accordance with the status indicated in the update (either displaying the data as stale or real-time).

FIG. 6 illustrates a method for monitoring the health (real-time availability) of financial 15 data transmitted from one or more data collection systems to one or more client site terminals in accordance with the present invention. This method-includes the steps of:

601: receiving real-time financial data from one or more data sources at a data collection system;
602: formatting the real-time financial data received from the data sources to include a system identifier corresponding to the data collection system;
603: generating a heartbeat signal including the system identifier;
604: transmitting the formatted real-time financial data to one or more client site terminals upon receiving corresponding requests from the client site terminals;
605: periodically transmitting the heartbeat signal to the one or more client site terminals upon receiving corresponding requests from the client site terminals;
606: receiving the requested real-time financial data from a data source at the client site terminal;
607: extracting the system identifier from the received real-time financial data;
608: comparing the extracted system identifier with stored status data to determine whether the client site terminal is monitoring the status of the data collection system;
609: if the status of the data source is not being monitored, transmitting a request to the data collection system to obtain the heartbeat signal for the system;
610: once the heartbeat signal for the system is received, displaying the real-time financial data in a real-time display mode;
611: determining whether the heartbeat signal was received during a predetermined period of time;
612: if the heartbeat signal was timely received, displaying the financial data received from the data collection system in a real-time (current) display mode and repeating the determining step of 611; and,
613: if the heartbeat signal was not timely received, displaying the financial data received from the data collection system in a stale (non-current) display mode and repeating the determining step of 611.

According to alternate embodiments of the data health monitor according to the present invention, additional display modes may be used. For example, financial data displayed by the client site terminals may be displayed in a real-time display mode, a stale display mode, or an unknown display mode (indicating to the user that the financial data is questionable). Moreover, in some embodiments of the present invention, both monitoring functions may be manually and independently activated and deactivated by the user at the client site terminal, for example, if the client site terminal has limited processing capacity and the user desires increased processing and display functions.

Furthermore, when financial data for a particular instrument includes both real-time and historical data, the data health monitor according to the present invention may be provided at the field level within each financial data record such that some fields are displayed as either real-time or stale data while others are displayed only as historical data This functionality may be implemented, for example, through the addition of one or more fields of identifier data within each financial data record.

While the present invention has been particularly described with reference to the preferred embodiments, it should be readily apparent to those of ordinary skill in the art that changes and modifications in form and details may be made without departing from the spirit and scope of the invention. It is intended that the appended claims include such changes and modifications.

We claim:

1. A method of identifying non real-time data transmitted through a communications network, the method comprising:
receiving at a data processor data from a data source of a plurality of data sources;
formatting the data to include a data source identifier corresponding to the data source and a system identifier corresponding to the data processor;
transmitting the formatted data to a client site via the communications network;
determining the operational status of the data source;
generating a data source status signal including the data source identifier, the data source status signal being generated based on the operational status of the data source; and
transmitting the data source status signal to the client site via the communications network.

2. The method of claim 1 wherein the step of generating a data source status signal includes determining whether the data source is operating normally.

3. The method of claim 1, further comprising receiving a heartbeat signal from the data source.

4. The method of claim 1, further comprising:
generating a system heartbeat signal including the system identifier; and
transmitting the system heartbeat signal at a predetermined interval to the client site.

5. The method of claim 4, wherein the system heartbeat signal includes a data source heartbeat signal received from the data source.

6. A data collection system comprising:
   a transmitter in communication with a communications network; and
   a data processor in communication with the transmitter, the data processor programmed to perform steps comprising:
      receiving data from a data source of a plurality of data sources;
      formatting the data to include a data source identifier corresponding to the data source and a system identifier corresponding to the data processor;
      transmitting via the transmitter the formatted data to a client site via the communications network;
      determining the operational status of the data source;
      generating a data source status signal including the data source identifier, the data source status signal being generated based on the operational status of the data source; and
      transmitting via the transmitter the data source status signal to the client site via the communications network.

7. The data collection system of claim 6 further comprising a status code generator generating a data source status signal in response to a control signal from the data processor, wherein the step of generating a data source status signal includes automatically generating the control signal for the status code generator in response to changes in the operating status of said data source.

8. The data collection system of claim 6, wherein the step of generating a data source status signal includes determining whether the data source is operating normally.

9. The data collection system of claim 6, wherein the data processor further performs the step of receiving a heartbeat signal from the data source.

10. The data collection system of claim 6 further comprising a heartbeat generator for generating a system heartbeat signal including the system identifier and transmitting via the transmitter the system heartbeat signal at a predetermined interval to the client site via the communications network.

11. The data collection system of claim 10 wherein the system heartbeat signal includes a data source heartbeat signal received from the data source.

12. A computer-readable medium having computer-readable instructions for causing a computer to perform steps comprising:
   receiving at a data processor data from a data source of a plurality of data sources;
   formatting the data to include a data source identifier corresponding to the data source and a system identifier corresponding to the data processor;
   transmitting the formatted data to a client site via a communications network;
   determining the operational status of the data source;
   generating a data source status signal including the data source identifier, the data source status signal being generated based on the operational status of the data source; and
   transmitting the data source status signal to the client site via the communications network.

13. The computer-readable medium of claim 12 wherein the step of generating a data source status signal includes determining whether the data source is operating normally.

14. The computer-readable medium of claim 12, the computer-readable instructions for performing the further step comprising receiving a heartbeat signal from the data source.

15. The computer-readable medium of claim 12, the computer-readable instructions for performing further steps comprising:
   generating a system heartbeat signal including the system identifier; and
   transmitting the system heartbeat signal at a predetermined interval to the client site.

16. The computer-readable medium of claim 15, wherein the system heartbeat signal includes a data source heartbeat signal received from the data source.

* * * * *